(12) United States Patent
Moulis

(10) Patent No.: US 7,204,824 B2
(45) Date of Patent: Apr. 17, 2007

(54) MEDICAL LIQUID DELIVERY DEVICE

(76) Inventor: Harry Moulis, 83 N. Saint Andrews Dr., Ormond Beach, FL (US) 32174

( * ) Notice: Subject to any disclaimer, the term of this patent is extended or adjusted under 35 U.S.C. 154(b) by 2 days.

(21) Appl. No.: 10/629,527

(22) Filed: Jul. 29, 2003

(65) Prior Publication Data
US 2005/0025798 A1 Feb. 3, 2005

(51) Int. Cl.
*A61M 31/00* (2006.01)
(52) U.S. Cl. ............ 604/93.01; 604/500; 604/290
(58) Field of Classification Search .......... 604/121, 604/96.01, 11–18, 286, 1–3, 317–416, 93.01, 604/158–159, 500, 164.01, 164.02, 164.04, 604/164.07, 171, 181, 182, 185, 187, 285, 604/287, 289, 290, 95.04, 104, 528; 600/201, 600/205, 215; 424/424, 423; 606/13
See application file for complete search history.

(56) References Cited

U.S. PATENT DOCUMENTS

| | | | | |
|---|---|---|---|---|
| 1,131,349 A | * | 3/1915 | Ellis | 604/15 |
| 1,909,967 A | * | 5/1933 | Jones | 604/1 |
| 3,592,192 A | * | 7/1971 | Harautuneian | 604/165.01 |
| 3,800,781 A | * | 4/1974 | Zalucki | 600/562 |
| 4,023,559 A | * | 5/1977 | Gaskell | 600/572 |
| 4,347,846 A | * | 9/1982 | Dormia | 606/127 |
| 4,424,054 A | * | 1/1984 | Conn et al. | 604/11 |
| 4,730,949 A | * | 3/1988 | Wilson | 401/132 |
| 4,952,204 A | * | 8/1990 | Korteweg | 604/1 |
| 6,221,096 B1 | * | 4/2001 | Aiba et al. | 623/1.11 |
| 6,290,677 B1 | * | 9/2001 | Arai et al. | 604/183 |
| 6,306,125 B1 | * | 10/2001 | Parker et al. | 606/1 |
| 6,599,296 B1 | * | 7/2003 | Gillick et al. | 606/108 |
| 6,692,458 B2 | * | 2/2004 | Forman et al. | 604/93.01 |
| 6,695,834 B2 | * | 2/2004 | Gellman et al. | 606/2.5 |
| 6,695,859 B1 | * | 2/2004 | Golden et al. | 606/184 |
| 6,702,759 B2 | * | 3/2004 | Pevoto | 600/562 |
| 6,793,648 B2 | * | 9/2004 | Oslund et al. | 604/160 |
| 2002/0082552 A1 | * | 6/2002 | Ding et al. | 604/103.02 |
| 2003/0032936 A1 | * | 2/2003 | Lederman | 604/507 |
| 2003/0073979 A1 | * | 4/2003 | Naimark et al. | 604/891.1 |
| 2003/0129183 A1 | * | 7/2003 | Spillert et al. | 424/94.64 |
| 2004/0236186 A1 | * | 11/2004 | Chu | 600/215 |

\* cited by examiner

*Primary Examiner*—Nicholas Lucchesi
*Assistant Examiner*—Theodore J. Stigell
(74) *Attorney, Agent, or Firm*—Timothy H. Van Dyke; Beusse Wolter Sanks Mora & Maire

(57) ABSTRACT

Disclosed herein are novel liquid delivery catheters, and methods and kits implementing the same. The disclosed catheters are particularly useful for localized delivery of a liquid caustic agent to treat various defects associated with malformations and injuries resulting in chronic or acute bleeding, or to ablate tumors, occlude fistulae or other luminal structures. The disclosed devices have uses in a number of medical disciplines, and specific examples are provided pertaining to treatment of defects, malformations, and injuries, or bleeding due to medical procedures, in and along the gastrointestinal tract.

16 Claims, 6 Drawing Sheets

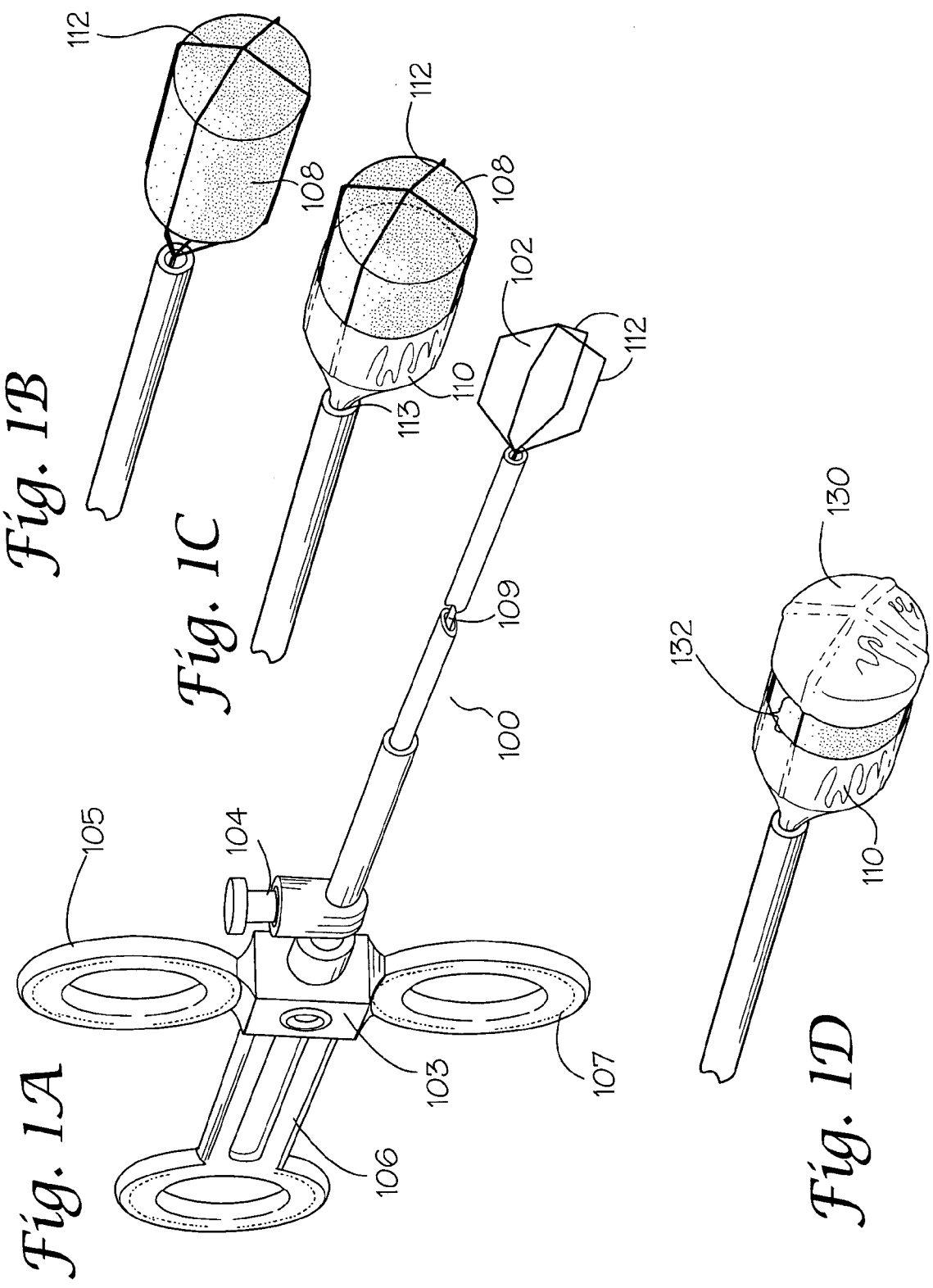

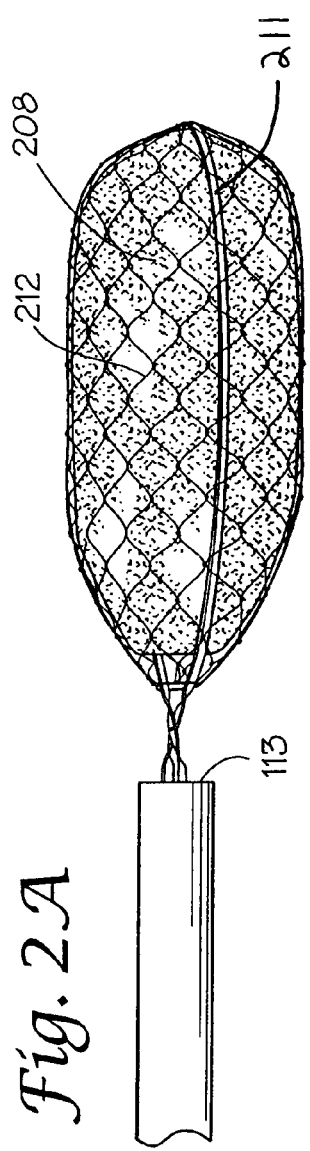
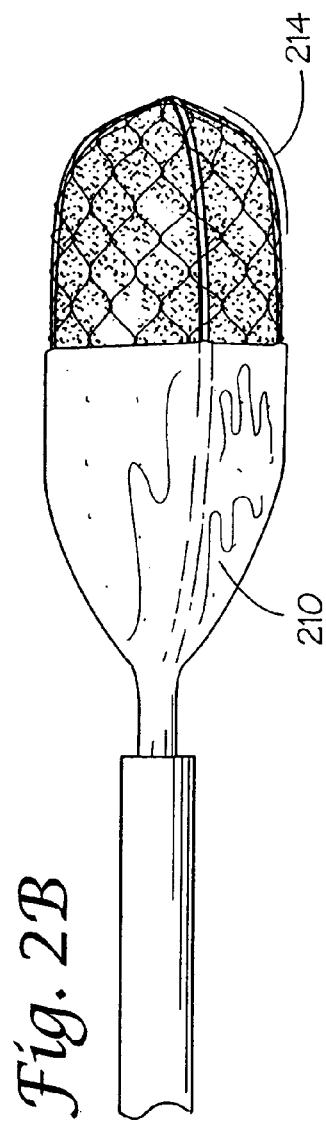
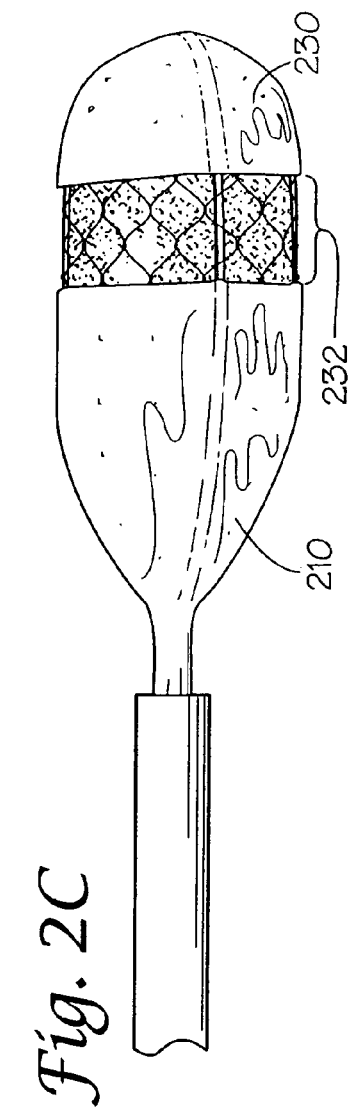

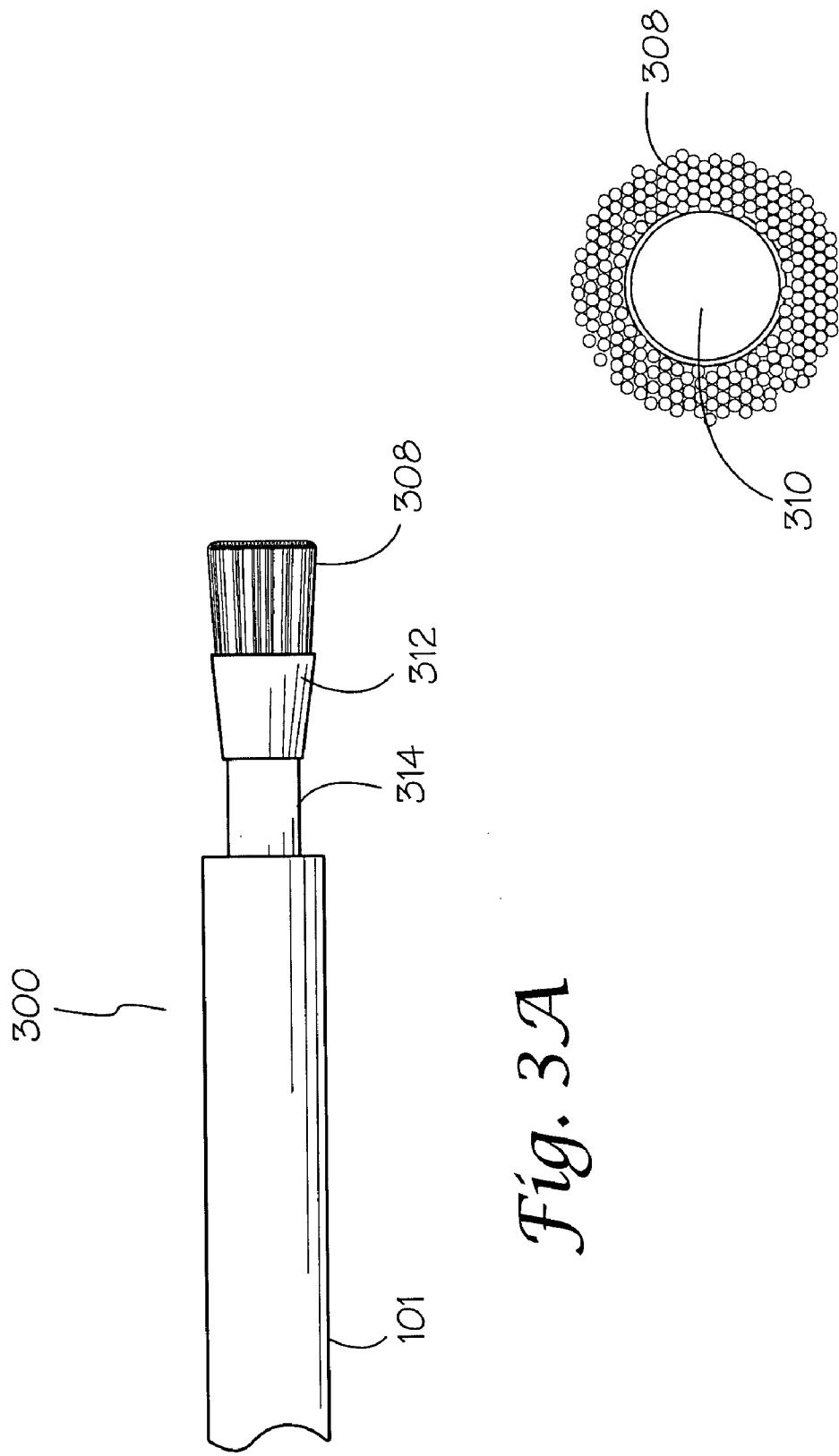

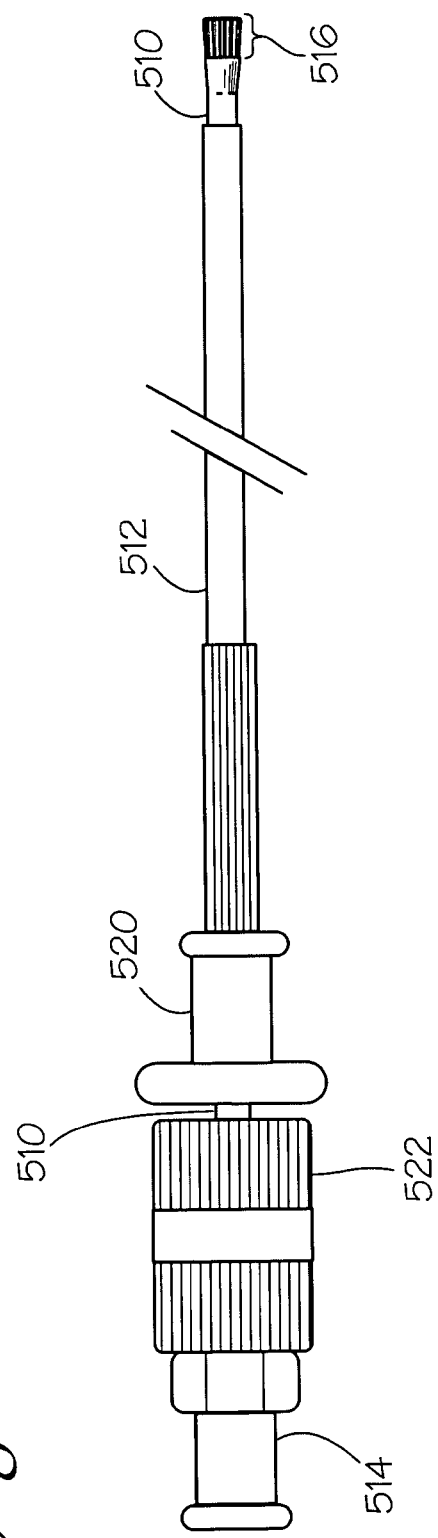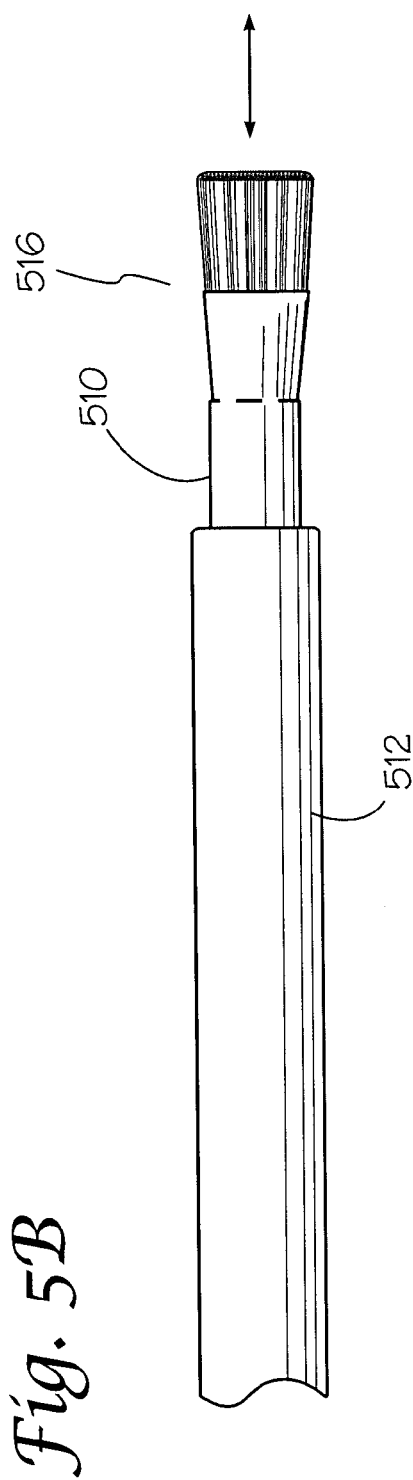
Fig. 5A
Fig. 5B

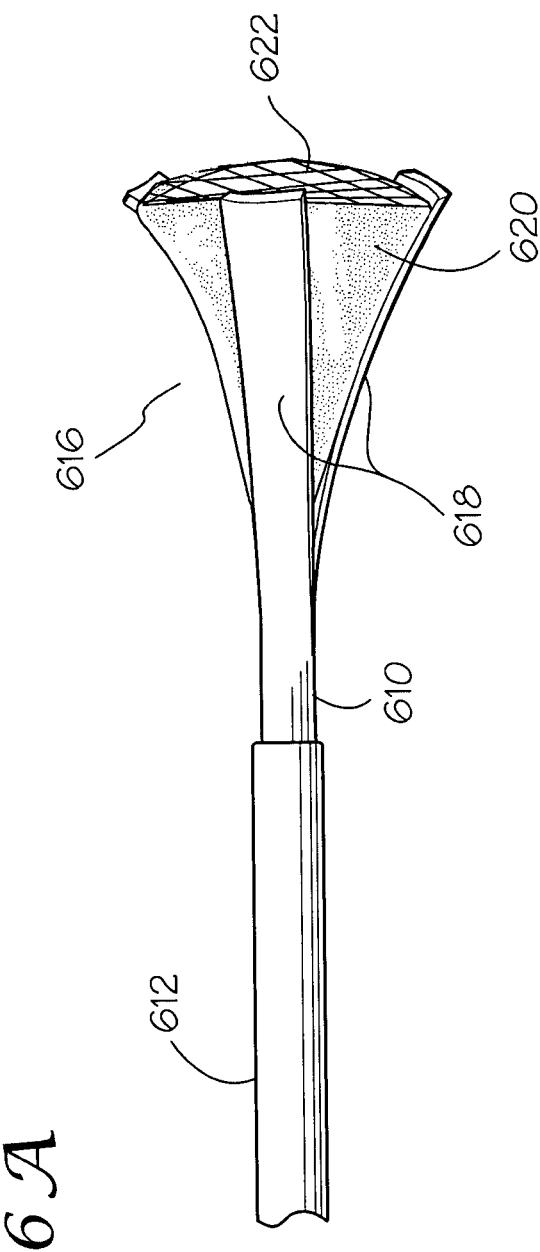
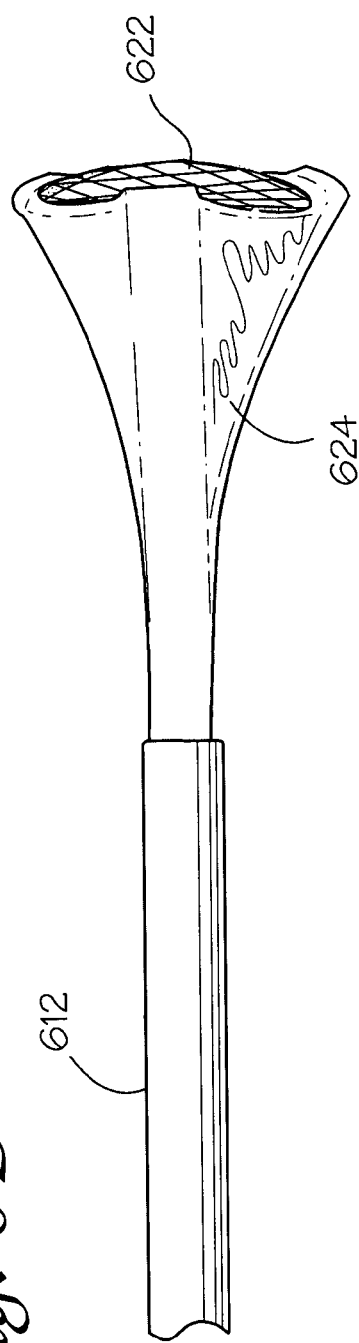
Fig. 6A
Fig. 6B

MEDICAL LIQUID DELIVERY DEVICE

BACKGROUND OF THE INVENTION

There are a number of vascular malformations, defects, or injuries that commonly occur along the lining of the intestine, parts of the gastrointestinal tract or urogenital pathways. Some of the more common types include angiodysplasias or telangiectasias (esophageal, gastric, duodenal, jejunal, ileal, colonic, rectal; Helmrich et al., *Southern Medical Journal* 83:1450–1453 (1990)), watermelon stomach (Gretz and Achem, *Am. J. Gastroentero.* 93:890–895 (1998); Binmoeller and Lieberman, *Gastrointest Endosc* 37:192–193 1991); gastric antral vascular ectasias, and radiation injury (radiation proctitis, esophagitis, gastritis, enteritis). A typical characteristic of these types of disorders is undesired bleeding (Lewis, *Gastroenterology Clinics of North America* 23:67–91; and Jaspersen et al., *Gastrointest Endosc* 40:40–44 (1994)). Indeed, gastrointestinal bleeding accounts for at least 2% of all hospital admissions each year (Levy, *N. Engl. J. Med* 290:1158 (1974)).

Conventional treatment of the foregoing disorders includes thermal treatment (Jensen et al. *Gastointest Endosc* 45:20–25 (1997); Askin and Lewis, *Gastrointest Endosc* 43:580–583 (1996), Argon Plasma coagulation (Wahab et al., Endoscopy 29:176–181 (1997), direct pressure (Kirollos, M. *J. Urology,* 1998 August 160:477–478; Hirokazu, T. *J. Urology,* 1998 November 160,:1803); and/or laser treatment (Taylor et al., *Gastrointest Endosc* 52:353:357 (2000)). However, these conventional methods are not without their drawbacks. The medical equipment is relatively costly and can be cumbersome to use. Furthermore, they present the potential risks of perforation (Pierzchajilo, *Colonoscopy,* 22:451–470 (1995); Bedford et al., *Am J Gastroenterol.,* 87:244–247 (1987)), or in the case of thermal treatment, heart disrhythmias or even colonic explosions (Monahan et al, *Gastrointest Endosc* 38:40–43 (1992); Vellar et al., *Br. J. Surg.* 73:157–158 (1986); Donato and Memeo, *Dis Colon Rectum* 36:291–292 (1993); Shinagawa et al., *Br. J. Surg.* 72:306 (1985)). Argon plasma coagulation has been shown to cause inflammatory polyps (Schmeck-Lindenau and Heine, *Endoscopy* 30:93–94 (1998). Further, direct pressure may be insufficient to achieve lasting hemostasis (Hirokazu, T. *J. Urology,* 1998 November 160:1803).

U.S. Pat. Nos. 6,187,346 and 6,165,492 to Neuwirth et al. disclose chemical cauterization devices and methods used for treatment of lesions occurring in the uterus. The system taught in these patents involves filling the uterus with a caustic agent, such as silver nitrate, and then neutralizing the cauterizing agent with a sodium chloride solution. However, the methods taught in U.S. Pat. Nos. 6,187,346 and 6,165,492 are not applicable to situations where filling a cavity, such as a uterine cavity, is not possible. Furthermore, these patents do not teach devices that control delivery of a caustic agent as to allow for controlled treatment of a limited area of tissue.

In view of the problems associated with traditional treatments, there is a need in the art for a cautery method that overcomes these problems, and provides an easy to use, inexpensive system for cauterization. While gastroenterologists encounter a number of chronic bleeding disorders, other medical disciplines, such as otorhinolaryngology, pulmonology, gynecology, urology, general surgery, thoracic surgery, and orthopedic surgery, may encounter deformations, defects, and/or injuries that result in undesired bleeding as well. Ideally, the new cautery method would be readily adaptable for use in medical procedures in the GI tract but also other organ systems. For example, transurethral resection of the prostate, or retropubic prostatectomy may lead to massive bleeding and an inability to achieve hemostasis in some patients (Touyama H. *J. Urology,* 1998 November 160:1803; Kirollos. M. *J. Urology* 1998 August 160:477–478). Studies related to these types of surgeries have discussed the problems of severe intra-operative bleeding. In most instances arterial bleeding can be controlled through electrocoagulation, whereas venous bleeding can be controlled by placing the catheter on traction and over-inflating the catheter balloon to create pressure sufficient to stop bleeding and promote coagulation. However, not all bleeding is of arterial origin and catheter traction to reduce post-operative venous bleeding only works when applied, having no effect after removal. (Walker E M. et al *Br. J. Urol* 1995 May: 75(5):614–7) In those patients with severe arteriovenous malformation, these procedures are insufficient to achieve complete hemostasis, leading to continued blood loss which may become life threatening. (Touyama, H. *J. Urology* 1998 November 160:1803). The double lumen catheter of the present invention solves this problem.

SUMMARY OF THE INVENTION

The subject invention is directed to a novel cautery system which provides localized cauterization and is easily adaptable for implementation in a number of surgical and non-surgical procedures. U.S. patent application Ser. Nos. 09/808,368; 09/882,811; and 09/899,556 discuss novel liquid delivery systems to deliver substances at a specific localized level. The subject invention also provides a novel liquid delivery system that can deliver substances, but with an emphasis on treating broader regions. The subject catheter delivery system comprises an end configured to accomplish controlled localized delivery of a caustic agent to a broader area. This invention modifies and adds to known retrieval devices such that they become liquid cautery (or other medicaments, drugs, gels, etc.) delivery devices. This liquid delivery catheter system can treat areas, in a controlled fashion, ranging from 3 $mm^2$ to 150 $mm^2$ or more. Preferably, it can treat an area having a size of approximately 10 to 100 $mm^2$.

According to a specific aspect, the subject invention pertains to a liquid delivery catheter comprising a proximal end and a distal end, and which comprises a retractable device that is retracted and extended out the distal end of said liquid delivery catheter. The retractable devices which may be implemented include, but are not limited to, a retractable basket, a retractable net, a retractable tripod or a retractable brush. In a preferred aspect, the retractable device comprises a liquid loadable means that may be loaded with a liquid and may release a liquid upon application of pressure or slight contact to said liquid loadable means.

According to a further aspect, the subject invention pertains to a method of delivering a caustic agent utilizing the cautery device of the subject invention. The subject method can be used to treat various malformations, defects, and injuries, while preventing bleeding risks commonly associated with surgical procedures.

In another aspect, the subject invention pertains to a non-surgical, non-steroidal method of contraception.

In yet another aspect, the subject invention pertains to a kit comprising the delivery catheter of the subject invention, a volume of a medical agent, preferably provided in a separate container.

These and other advantageous aspects of the subject invention will be described in further detail below.

DESCRIPTION OF THE DRAWINGS

FIG. 1 show a perspective view of a first embodiment of the subject invention that comprises a delivery catheter comprising a retractable basket. FIG. 1A relates to a prior art retrieval device comprising a retractable basket. FIG. 1B shows a delivery catheter comprising a squeezable material positioned within the retractable basket. FIG. 1C shows the embodiment of FIG. 1B further comprising a liquid impermeable coating to minimize spillage of the delivered agent. FIG. 1D shows an embodiment that is specifically suitable for certain lesions that also comprises an end coating.

FIG. 2 shows a side view of a second embodiment of the subject invention that comprises a retractable net. FIG. 2A shows the retractable net that has positioned within a squeezable material that holds liquid. FIG. 2B shows the retractable liquid delivery net that comprises a liquid impermeable barrier to minimize spillage of the liquid agent. FIG. 2C shows an embodiment that is specifically designed for certain lesions that also includes an end coating.

FIG. 3 shows a third embodiment of the subject liquid delivery catheter that comprises a retractable liquid delivery brush. FIG. 3A shows a side view. FIG. 3B shows an end view.

FIG. 4 shows an embodiment of the subject liquid delivery catheter comprising a retractable tripod.

FIG. 5 shows another embodiment of the subject liquid delivery catheter that comprises an inner and an outer catheter, and wherein the inner catheter comprises a luer-lok or snap-fit proximal end. FIG. 5A represents a side view of the entire embodiment. FIG. 5B shows a closed up of the embodiment shown in FIG. 5A.

FIG. 6 shows an alternate version of the prong embodiment shown in FIG. 4. FIG. 6A represents a side view of the prong assembly without a barrier. FIG. 6B shows a side view of the prong assembly with a barrier.

DESCRIPTION OF THE PREFERRED EMBODIMENTS

Figure 4A:
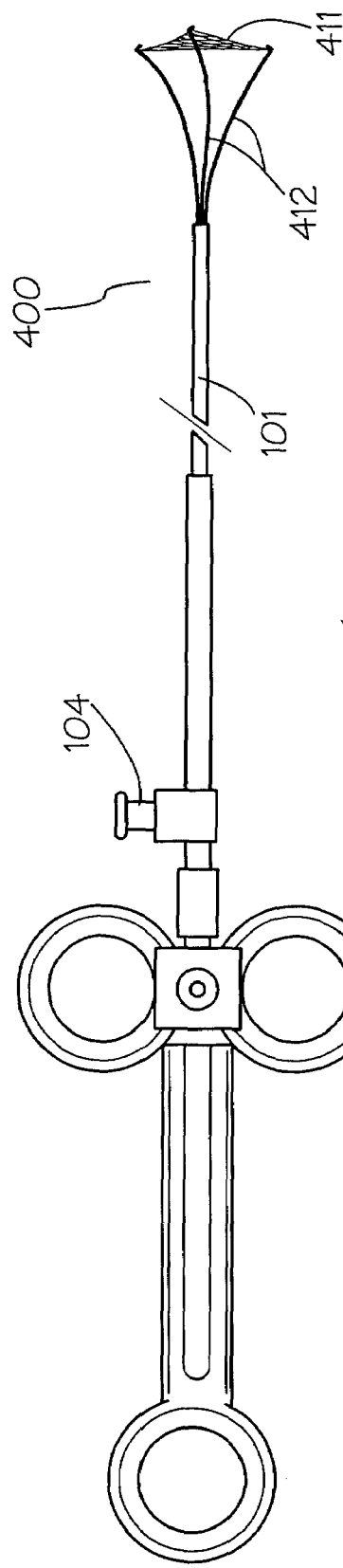
FIG. 4A shows a retractable tripod embodiment with a mesh barrier on its end.

As discussed above, the subject invention is directed to medical devices useful as a liquid delivery system, and specifically for delivering a caustic agent to a site of need. Turning to the drawings, FIG. 1 shows an embodiment of the subject liquid delivery catheter embodiment 100. The catheter 100 comprises a retractable basket 112. The retractable basket 112 is extended and retracted based on pushing the handle stock 106 into or out of the handle base 103. The extending and retracting of the retractable basket 112 is effectuated by a mechanical interlink 109 disposed within the catheter 100 which is attached to or integrated with the retractable basket. Handle grips 105 and 107 assist the user in holding the catheter embodiment 100 during retraction, extension, and liquid delivery. As shown in FIG. 1B, the retractable basket 112 has disposed within a squeezable material 108 capable of holding a liquid, such as a sponge, gauze or like material. The retractable basket 112 may be retracted or extended with the squeezable material 108 in place. Preferably, the catheter embodiment 100 is used to delivery a caustic agent to a site of need. Accordingly, FIG. 1C shows the catheter embodiment 100 with a liquid impermeable barrier 110 surrounding the retractable basket 112. The barrier 110 may be made of plastic or like material that possesses the requisite flexibility necessary to allow retraction and extension of the retractable basket 112. The barrier 110 minimizes the spillage and dripping of liquid agent out of the end 113 of the catheter embodiment 100. The barrier 110 may cover the retractable basket 112 at varying degrees. For example, though not shown, the barrier 110 may cover the basket up to the end portion of the retractable basket 112, similar to the embodiment shown in FIG. 4C. During liquid delivery, a liquid agent is injected into injection port 104 which travels down the length of the catheter 100 and exits out the end 113 thereby wetting the squeezable material 108. During use, the end of the retractable basket 112, in an extended state, is contacted to the site of need thereby delivering a liquid agent. Discussed infra is the utilization of a scope to facilitate the utilization of the subject liquid delivery catheter. The embodiment 100 may also comprise an end barrier 130, thereby exposing a region 132 between barriers 110 and 130 out of which liquid agent may be delivered (see FIG. 1D). The catheter is advanced through the working channel of the endoscope (gastroscope, enteroscope, colonoscope, hysteroscope, etc.). Extraction baskets known in the art which can be modified in accordance with the teachings herein include, but are not limited to, MEMORY BASKETS and WEB Extraction Basket (Wilson-Cook Medical, MSB-xx; MB5-xx; WEB-xx); BARD® Tripod Forceps Sets and Basket Sets; Olympus Endo-Therapy® Stone Retrieval Baskets, Retrieval Baskets, Grasping Forceps, and Mechanical Lithotriptors.

Shown in FIG. 2A is an alternative configuration of the delivery catheter shown in FIG. 1. FIG. 2A depicts a retractable net 200 embodiment which comprises a net or mesh 212 that may be extended and retracted in conjunction with the liquid delivery catheter described in FIG. 1: the retractable basket of FIG. 1 is replaced with a retractable net 212. The retractable net comprises a squeezable material 208, such as a sponge, gauze, or like material. The net is supported by a support wire 211, which facilitates the ejecting and retracting of the retractable net 212. Liquid agent is delivered to retractable net embodiment 200 out the end of the catheter 113. Similar to the embodiment shown in FIG. 1, the retractable net may comprise a liquid impermeable barrier 210 (see FIG. 2B). This barrier 210 is especially important when delivering agents, such as caustic agents, where it is desirous to minimize exposure to healthy, non-targeted tissue. The barrier 210 may cover the retractable net at varying degrees. In one embodiment, not shown, the barrier 210 extends to the end of the net embodiment 200, such that only the end of the net is exposed, similar to the embodiment shown in FIG. 4C. The liquid agent is delivered to the retractable net embodiment 200 such that the squeezable material 208 is sufficiently wetted, and is then delivered by contacting the non-covered end 214 with the targeted area in the patient. The embodiment 200 may also comprise an end barrier 230, thereby exposing a region 232 between barriers 210 and 230 out of which liquid agent may be delivered (see FIG. 2C).

FIG. 3 shows a retractable brush embodiment 300 that may be adapted for use with the basic liquid delivery catheter 100 shown in FIG. 1 (naturally, the retractable net 212 would be replaced by the retractable brush embodiment 300). The retractable brush embodiment comprises bristles 308, a bristle base 312, and stem 314. FIG. 3B shows an end view of the embodiment 300, which shows the lumen 310 for delivering liquid agent to the brush. The liquid agent wets the bristles 308. Upon wetting, the retractable brush 308 can treat the area of need by contacting the brush 308 with the targeted area. With controlled movements of the endoscope, broad surface areas may be "painted" with the caustic agent.

Figure 4B:
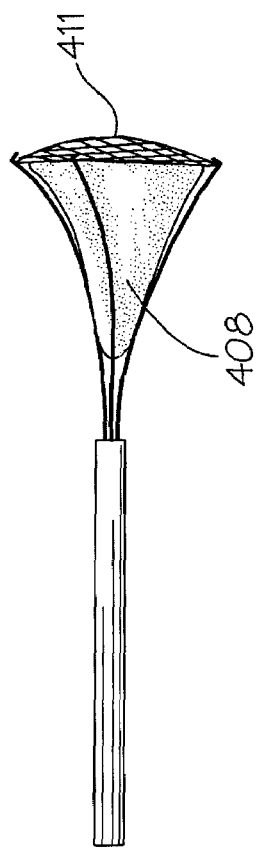
FIG. 4B shows the embodiment shown in FIG. 4A that further comprises a squeezable material capable of holding a liquid agent.
Figure 4C:
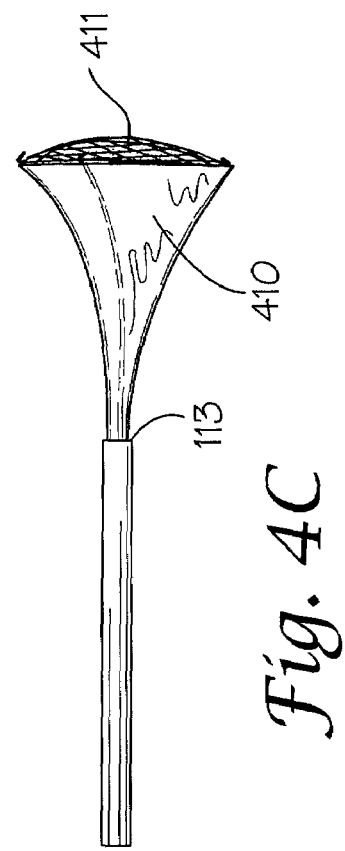
FIG. 4C shows the embodiment of FIG. 4B that further comprises a liquid impermeable barrier on the exterior to minimize spillage of the liquid agent.

In FIG. 4, a retractable tripod embodiment 400 is shown. The retractable tripod embodiment 400 may be used in conduction with a liquid delivery catheter, such as that described for FIG. 1, supra. Naturally, the retractable basket embodiment 100 is replaced with the retractable tripod embodiment 400. As shown in FIG. 4A, the retractable tripod embodiment 400 comprises flexible support wires 412. At the end of the support wires 412 is attached a mesh or net 411. In FIG. 4B, a squeezable material 408 is shown disposed in the space formed by the support wires 412. As discussed supra, the squeezable material 408 is capable of holding liquid. In FIG. 4C, a liquid impermeable barrier 410 is added to the exterior of the retractable tripod 400. This barrier minimizes the spillage of liquid agent. During use, the retractable tripod is extended from the end of the catheter 113. A liquid agent is injected into the catheter at port 104. The liquid travels down the elongated body 101 of the catheter and out the end 113 of the catheter. The squeezable material 408 becomes wetted by the liquid agent. Once sufficiently wetted, an area of need may be treated by contacting the end of the retractable tripod with the targeted area. A tripod is shown with three flexible support wires (members); however, those skilled in the art will appreciate that three or more wires may be used in the retractable tripod embodiment.

Turning to FIG. 5, a different catheter embodiment 500 is shown which is configured without a handle. Embodiment 500 comprises an inner catheter 510 and an outer catheter 512. Affixed to the proximate end 514 of the inner catheter 510 is a Luer-lok or snap fitting to preferably connect to a syringe (not shown). The distal end 516 of the inner catheter 510 comprises a brush end similar to that shown in FIG. 3. The distal end 516 may be extended and retracted through the outer catheter 512 by pushing and pulling the proximate end 514 of the catheter. At the proximate end of the outer catheter 512 is a stop base 520 which abuts handle base 522 of the inner catheter 510. The handle base 522 aids in manipulating the inner catheter 510, and the stop base 520 prevents overextension of the distal end 516. FIG. 5B is a close-up view of the distal end 516.

FIGS. 6A–B shows an alternative retractable tripod embodiment 600. This embodiment may be designed with an inner and outer catheter similar to that in FIG. 5 or with implementation with a mechanical interlink and handle according to that shown in FIG. 4. Preferably, as is shown, embodiment 600 comprises an inner catheter 610 and an outer catheter 612. The distal end of the inner catheter 616 is cut or formed so as to form a prong assembly 618. The prong assembly preferably has at least three support members (or prongs). The prongs actually correlate to and are integral with the wall structure of the inner catheter 610. This design may be more cost-effective and easier to make, as the prong assembly 618 can be formed by simply cutting the distal end of the inner catheter 616. Similar to that shown in FIG. 4, a liquid loadable means 620 is positioned in the space between the prongs. A mesh 622 is provided at the tip of the prong assembly to allow delivery of fluid agent. A fluid impermeable barrier 624 is disposed around the prong assembly 618.

A number of conventional materials commonly used in the medical industry can be used to make subject liquid delivery catheter. Examples of such materials include, but are not limited to, polyvinyl chloride, polyethylene, polypropylene, polyethylene terephthalate, polyurethane, polytetrafluoroethylene, fluoroethylenepropylene, or nylon, or combinations thereof. Examples of suitable materials are disclosed, e.g., in U.S. Pat. Nos. 6,165,166; 4,707,389, 3,561,493. The structural properties of the subject liquid delivery catheter will be dictated by the intended use. For example, use of the subject liquid delivery catheter with a flexible endoscope will require that the catheter is also flexible. Those skilled in the art will readily recognize appropriate materials for making such catheters to meet this requirement, as well as in the case where there is a need for a more rigid catheter.

The squeezable material useful in accordance with the teachings herein can be any material that can be loaded and hold a liquid and then release the liquid upon contact/pressure on the material. The squeezeable material may include, but is not limited to, sponges made of appropriate material, gauze, cotton balls and like materials. Those skilled in the art will readily recognize that vast variety of materials that could be used, so long as such materials can hold a liquid and release a liquid upon contact with the material.

The subject cautery device has a number of applications, in a number of different medical disciplines. With respect to gastroenterology, the subject invention may be useful to treat, for example, vascular malformations, watermelon stomach, gastric antral vascular ectasias, radiation injury, benign neoplasms, post-polypectomy bleeding, post-endoscopic ampullary sphincterotomy bleeding, ulcers, Dieulafoy's lesions, benign or malignant neoplasms, Barrett's esophagus with or without dysplasia, varices, bleeding Mallory-Weiss tears, as well as to ablate malignant or hemorrhagic neoplasms. Additionally, it may be used to abate bleeding from portal hypertensive gastropathy or colitis, or for fistula occlusion. With respect to urology, the subject invention may be useful to treat, for example, chronic bleeding associated with retropubic prostatectomy, transurethral resection of the prostate, and other complications associated with urogenital surgical procedures. With respect to gynecology, the subject invention may be useful in treating lesions in the endocervical canal, such as uterine polyps.

Alternatively, the procedure may be used as a safe effective method of contraception. Over the past 30 years, interest in population control and personal choice has led to a dramatic increase in the use of contraceptive methods, including voluntary sterilization, insertion of intra-uterine devices (IUD), administration of pills, and insertion of implants to avoid unplanned or unwanted childbearing. Female sterilization has become the most prevalent method of fertility regulation accounting for one-third of all contraceptive use worldwide. (Cooper J. *Clinical Obstetrics and Gynecology* 1992 35(2) 282–298). However, traditional tubal sterilization methods have been implicated in maternal death because the risky procedure often requires major surgery, anesthesia or both. (Shuber, J *Am J Obstet Gynecol* 1989 April: 160(4): 887–889) The present invention addresses the need for a safer, simpler non-surgical, non-hormonal sterilization procedure. Through direct application of a caustic sclerosing substance, complete tubal occlusion in an outpatient setting may be achieved. The efficacy of such a procedure has been studied in humans and animals. Shuber. J (*Am J Obstet Gynecol* 1989 April:

160(4):887–889) administered Methyl 2-cyanoacrylate to the uterocornual tubal junction in 35 healthy, parous women. Hysterosalpingography 4 months after the procedure showed bilateral tubal occlusion in 88.2% of the study participants. No complications were reported and there were no pregnancies reported in those participants who demonstrated tubal occlusion. In another study, the uterotubal junction (UTJ) in rabbits was destroyed using bipolar electrical current, and a plug containing either quinacrine or platelet extract was inserted. Histologic assessment by serial sections indicated occlusion of the UTJ in 96% of the rabbits treated.(Vancaillie, T G et al. *Fertil Steril* 1989 February, 51(2):335–8) The present method differs from these two examples in the materials used and the mode of application, potentially making it a superior method of sterilization.

Examples of caustic agents appropriate for use with the teachings herein include, but are not limited to, silver nitrate, zinc chloride, copper sulfate, phenol, acids, alkali, iodine, absolute alcohol, potassium permanganate, formalin\or combinations thereof. Furthermore, depending on the intended use, the viscosity and strength or concentration of the selected caustic agent is routinely adjusted. Where deeper penetration of the caustic agent is preferred, a more concentrated solution of the caustic agent should be used. Other characteristics such as speed and severity of cautery are adjusted as well, depending on the desired use and may be achieved by altering viscosity.

The activity of the caustic agent is readily effective by using silver compounds such as silver nitrate and silver thiocyanate or other compounds which can release silver ions. The silver ions react with the sulfides, proteins, and chlorides in cells. Since the sulfides and chlorides are vital to cell metabolism, the reaction results in necrosis of the cells. Another potentially useful agent is iodine, which is radiopaque like silver. Compositions containing iodine react with the target tissue as the result of the release of elemental free Iodine and the reaction can be stopped by forming a stable compound, for example, sodium iodide, by instilling sodium chloride. In an especially preferred embodiment, silver nitrate and DEXTRAN 70 are utilized together because they are easy to work with, are controllable, and are recognized by the medical profession and government regulatory agencies as acceptable agents for human use. DEXTRAN 40 and 70 can be used intravenously and intramuscularly and in several organ systems such as the genital tract. Silver nitrate is used on the skin, upper respiratory tract, lower genital tract, and other locations. The silver ion has a loose but stable binding with the dextran carrier but is pulled off by the consumption of the ion at the tissue sites by binding to anions and protein. The carrier may be made of dextrans or glucose or other sugars used in intravenous solutions but preferably in concentrations sufficient to form gels or pastes. The compositions prepared in accordance with this invention have a viscosity that is suitable for their intended purpose at temperatures between about 20° C. and about 37° C., however, the viscosity may be adjusted as specific applications dictate. Alginates, aloe, carboxymethylcellulose, silicones and oxidized cellulose may also be used to form pastes and gels but the dextrans and sugars are the preferred choices because of their acceptance by the medical profession and regulatory agencies. Alternatively, the practitioner may use formalin as an inexpensive, effective treatment to control bleeding. Several studies have demonstrated the efficacy of topical formalin application in the treatment of hemorrhagic radiation induced proctitis to control bleeding (Seow-Choen, F. et al. *Dis Colon Rectum*, 1993 February 36(2)135–36; Saclarides, T. *Dis Colon Rectum* 1996 February 39(2):196–199)

The speed and severity of the chemical necrosis may be regulated by the percentage of the silver nitrate in the paste. By increasing the percentage of the silver nitrate in the paste the possibility for a deeper burn is increased. It is possible, by procedures well known to those skilled in the art, to determine the appropriate concentration of silver nitrate to achieve the desired depth of cauterization for specific applications. The practitioner may readily formulate a paste that is essentially self-regulating. For example, a weak silver nitrate paste may be formulated that will expend itself after necrosing to a depth of only half the maximum safely allowable depth, thereby reducing the danger of necrosing too deeply. Preferably, the composition comprises 1–50%, by weight, of caustic agent. More preferred, the caustic agent comprises 10–40%, by weight of the composition. Alternatively, the practitioner may easily terminate the treatment by introducing a normal saline solution, e.g., NaCl, which will deactivate the silver nitrate by forming silver chloride. An advantage of the silver nitrate is that the deactivating agent for the silver ion is the chloride ion found in several solutions used regularly in medicine, e.g., intravenously and intramuscularly, such as normal saline or Ringer's solution. The silver nitrate deactivation is the essentially stoichiometric formation of an insoluble non-caustic precipitate. The viscosity of the caustic composition may be adjusted so that it does not flow uncontrollably from the site of need. The caustic composition should flow easily, i.e, without excessive pressure, through a catheter having an inside diameter of about 1–2 mm. Preferably, the caustic composition should be thick enough that it does not run, i.e., it stays in the vicinity of the point of application. In a preferred embodiment, a caustic composition having a consistency ranging from toothpaste to pancake syrup is utilized as specific applications dictate. The ability to use a desired consistency will be limited only by the internal dimensions of the catheter employed. Thixotropic caustic compositions utilizing, e.g., mineral clays or the like may be especially useful in some applications. While modifying the viscosity of the cauterizing compound can alter the flow properties and therefore aid in the control of delivery, the subject cautery device allows for controlled delivery of a cauterizing agent having a broad range of viscosities.

EXAMPLE

Use of Catheter to Treat Lesion
   A lesion is identified endoscopically.
   The medical liquid (caustic agent) is drawn up into the syringe.
   The syringe is attached to the proximate end of the catheter at the injection port.
   The retractable device is extended beyond the outer catheter. The plunger of the syringe is gently pressed so that the medical liquid (caustic agent) fills the lumen of the (inner) catheter and soaks the liquid loadable means.
   The retractable device is retracted into the outer catheter.
   The catheter is advanced through the working channel of the endoscope so that it protrudes beyond the tip.
   The retractable device is extended.
   The liquid loadable means (LLM) is placed in contact with the lesion to be treated. The plunger of the syringe is gently pressed so that the LLM is moistened enough to allow the caustic agent to transfer from the LLM to the surface being treated.

The caustic agent may be dabbed repeatedly at one or more sites until the desired amount is delivered; this is determined by the change in appearance of the treated surface.

Alternatively, the LLM may be swept across the treatment surface by controlled movements of the endoscope.

Once application is completed, the syringe plunger is gently drawn back so that negative pressure draws residual caustic agent from the LLM into the inner catheter and/or syringe, thereby decreasing the risk of caustic agent inadvertently leaking onto normal tissue as the LLM (excluding brush design) is squeezed while it is being retracted into the outer catheter.

The catheter is withdrawn from the working channel of the endoscope.

The teachings of all patents and publications, including U.S. patent application Ser. No. 09/899,556, cited throughout this specification are incorporated by reference in their entirety to the extent not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A liquid delivery catheter comprising:
   a). a cannulated catheter comprising an elongated portion, said elongated portion comprising a proximal end and a distal end;
   b). a retractable device that is extended and retracted out the distal end of the catheter;
   c) a liquid impermeable barrier covering a portion of said retractable device thereby creating an exposed portion and covered portion of said retractable device when extended, said liquid impermeable barrier configured so as to provide fluid communication between said retractable device and said cannulated catheter; and
   d) a squeezable material disposed within said retractable device.

2. The liquid delivery catheter of claim 1, wherein said retractable device is connected to a mechanical interlink disposed within said liquid delivery catheter.

3. The liquid delivery catheter of claim 2, wherein said proximal end is attached to or integrated with a stock base; and further comprising a stock handle slidingly engaged to said stock base, wherein said mechanical interlink is conjoined to said stock handle such that upon sliding said stock handle into said stock base said retractable device is moved.

4. The liquid delivery catheter of 1, further comprising a liquid injection port disposed thereon such that liquid may be injected into said catheter and exuded out said distal end of said catheter to said retractable device.

5. The liquid delivery catheter of claim 1, wherein said retractable device is a retractable basket comprising at least one flexible support wire, said at least one flexible support wire configured such that it forms a closed support structure comprising a space for said squeezable material.

6. The liquid delivery catheter of claim 5, wherein said retractable device comprises at least three flexible support wires conjoined or integrated together at a distal apex.

7. The liquid delivery catheter of claim 1 wherein said retractable device comprises a retractable net comprising at least one flexible support guide.

8. The liquid delivery catheter of claim 7 further comprising a squeezable material disposed within said retractable net.

9. The liquid delivery catheter of claim 1 wherein said retractable device comprises a retractable tripod having a proximal end and a distal end, said retractable tripod comprising at least three flexible support members and a mesh attached to said at least three flexible support wires at the distal end of said retractable tripod.

10. The liquid delivery catheter of claim 9, wherein said retractable tripod comprises a squeezable material disposed in the space between at least three flexible support wires.

11. A liquid delivery catheter comprising:
   a) an outer cannulated catheter comprising a proximal end and a distal end;
   b) an inner cannulated catheter disposed within said outer cannulated catheter comprising a proximal end and a distal end
   c) a retractable device attached to or integrated with said distal end of said inner cannulated catheter that is extended and retracted out the distal end of said outer catheter, said retractable device comprising a brush that comprises at least one lumen in fluid communication with said inner cannulated catheter and wherein said brush comprises bristles for receiving and applying a fluid, the fluid distributed to said bristles from said lumen; and
   d) a syringe attached to said proximate end of said inner cannulated catheter.

12. The liquid delivery catheter of claim 11 wherein said brush comprises bristles configured substantially in arcuate manner around said at least one lumen.

13. A method of treating an area of need of a patient comprising obtaining the liquid delivery catheter of claim 1; wetting the retractable device with a liquid agent; applying the liquid agent to the area of need by contacting the retractable device to the area of need.

14. The method of claim 13, wherein the liquid agent is a caustic agent.

15. A method of treating an area of need of a patient comprising obtaining the liquid delivery catheter 11; wetting the retractable device with a liquid agent; applying the liquid agent to the area of need by contacting the retractable device to the area of need.

16. The method of claim 15, wherein the liquid agent is a caustic agent.

* * * * *